United States Patent
Hamada et al.

(10) Patent No.: US 12,162,832 B2
(45) Date of Patent: Dec. 10, 2024

(54) PRODUCTION METHOD OF ASYMMETRIC CHAIN CARBONATE

(71) Applicant: DAIKIN INDUSTRIES, LTD., Osaka (JP)

(72) Inventors: Tomohito Hamada, Osaka (JP); Michiaki Okada, Osaka (JP); Akiyoshi Yamauchi, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 433 days.

(21) Appl. No.: 16/881,997

(22) Filed: May 22, 2020

(65) Prior Publication Data

US 2020/0283370 A1   Sep. 10, 2020

Related U.S. Application Data

(63) Continuation of application No. 15/774,829, filed as application No. PCT/JP2016/084621 on Nov. 22, 2016, now Pat. No. 10,774,028.

(30) Foreign Application Priority Data

Nov. 24, 2015   (JP) .................... 2015-229018

(51) Int. Cl.
C07C 68/02   (2006.01)
C07C 69/96   (2006.01)

(52) U.S. Cl.
CPC .............. C07C 68/02 (2013.01); C07C 69/96 (2013.01)

(58) Field of Classification Search
CPC ................................ C07C 68/02; C07C 69/96
See application file for complete search history.

(56) References Cited

U.S. PATENT DOCUMENTS

| | | | |
|---|---|---|---|
| 5,659,062 A | 8/1997 | Yokoyama et al. | |
| 2007/0276151 A1 | 11/2007 | Lee et al. | |
| 2010/0094039 A1 | 4/2010 | Ooms | |
| 2012/0141870 A1* | 6/2012 | Chen ................. | H01M 10/0569 429/200 |
| 2015/0191414 A1* | 7/2015 | Bomkamp ............... | C07C 69/96 558/260 |
| 2016/0285131 A1 | 9/2016 | Yamauchi et al. | |
| 2016/0293997 A1 | 10/2016 | Yamauchi et al. | |

FOREIGN PATENT DOCUMENTS

| | | | | |
|---|---|---|---|---|
| CN | 101056841 A | 10/2007 | | |
| EP | 2 380 868 A1 | 10/2011 | | |
| GB | 629019 | 9/1949 | | |
| GB | 2 067 194 A | 7/1981 | | |
| JP | 06166660 A | 6/1994 | | |
| WO | 2004/024658 A1 | 3/2004 | | |
| WO | 2006/054833 A1 | 5/2006 | | |
| WO | WO-2009102069 A1 * | 8/2009 | ................ | C12P 7/62 |
| WO | WO-2014026431 A1 * | 2/2014 | ............. | C07C 68/02 |
| WO | 2014/165748 A1 | 10/2014 | | |
| WO | 2015/083745 A1 | 6/2015 | | |
| WO | 2015/083747 A1 | 6/2015 | | |
| WO | WO-2018073124 A1 * | 4/2018 | ........... | C07C 269/04 |

OTHER PUBLICATIONS

Yamamoto et al. WO 2009/102069 A1 English machine translation (online) obtained from <https://patentscope.wipo.int>. (Year: 2009).*
Chattaway et al. "n-Butyl Chloroformate and its Derivatives" J. Chem. Soc. Perkins Trans. 1920, 117, 708-711. (Year: 1920).*
Hasegawa et al. Regioselective Anodic Monofluorination of Ethers, Lactones, Carbonates, and Esters Using Ionic Liquid Fluoride Salts. J. Electrochem. Soc. 2006, 153, D162-D166. (Year: 2006).*
Zhang et al. WO 2014/026431 A1 English machine translation [online] retrieved on Jan. 13, 2024 from <https://patents.google.com/patent/WO2014026431A1/en?oq=WO+2014026431+> (Year: 2014).*
Yokoyama JP-06166660 (pub. 1994)—A English machine translation (obtained Mar. 27, 2020) (Year: 1994).
International Search Report for PCT/JP2016/084621 dated Feb. 21, 2017 [PCT/ISA/210].
International Preliminary Report on Patentability with the translation of the Written Opinion dated May 29, 2018, issued in corresponding International Application No. PCT/JP2016/084621.
Extended European Search Report dated May 20, 2019, from the European Patent Office in counterpart European Application No. 16868560.0.
Zhen-Zhen Yang et al., "Dimethyl carbonate synthesis catalyzed by DABCO-derived basic ionic liquids via transesterification of ethylene carbonate with methanol", Tetrahedron Letters, vol. 51, No. 21, May 1, 2010, pp. 2931-2934 (4 pages total).
Songlin Wang et al., "Preparation and catalytic property of $MoO_3$/$SiO_2$ for disproportionation of methyl phenyl carbonate to diphenyl carbonate", Elsevier Ltd, Journal of Molecular Catalysis A: Chemical, vol. 398, Nov. 24, 2014, pp. 248-254 (7 pages total).
Jaromir Mindl et al., "Alkoxycarbonylation of Alcohols and Phenols by Nitrosoformates", Collection Symposium Series (XIIIth Symposium on Chemistry of Nucleic Acid Components Spindleruv Mlyn, Czech Republic; Sep. 3-9, 2005), vol. 61, No. 7, Mar. 18, 1996, pp. 1053-1063 (11 pages total).

* cited by examiner

*Primary Examiner* — Amanda L. Aguirre
(74) *Attorney, Agent, or Firm* — Sughrue Mion, PLLC

(57) ABSTRACT

A method for producing an asymmetric chain carbonate by reacting an alcohol with a halocarbonate ester compound in the presence of a basic magnesium salt.

2 Claims, No Drawings

PRODUCTION METHOD OF ASYMMETRIC CHAIN CARBONATE

CROSS REFERENCE TO RELATED APPLICATIONS

This application is a continuation of U.S. application Ser. No. 15/774,829, filed May 9, 2018, which is a National Stage of International Application No. PCT/JP2016/084621, filed Nov. 22, 2016, which claims priority from Japanese Patent Application No. 2015-229018, filed Nov. 24, 2015, the disclosures of which are incorporated herein by reference in their respective entireties.

TECHNICAL FIELD

The present invention relates to a method for producing an asymmetric chain carbonate. The present invention also relates to a composition containing an asymmetric carbonate.

BACKGROUND ART

Patent Literature 1 reports production of methyl-2,2,2-trifluoroethyl carbonate with a yield of 46% by adding methyl chloroformate to a solution containing 2,2,2-trifluoroethanol, pyridine, and dichloromethane.

Patent Literature 2 and Patent Literature 3 describe production of highly purified methyl-2,2,2-trifluoroethyl carbonate by mixing trifluoroethanol, pyridine, and triglyme, and dropwise adding methyl chlorocarbonate to the mixture to synthesize methyl-2,2,2-trifluoroethyl carbonate, followed by rectification to collect highly purified methyl-2,2,2-trifluoroethyl carbonate.

CITATION LIST

Patent Literature

Patent Literature 1: US 2012/0141870
Patent Literature 2: WO 2015/083745
Patent Literature 3: WO 2015/083747

SUMMARY OF INVENTION

Technical Problem

Unfortunately, the conversion rate and selectivity are insufficient in conventional techniques using pyridine.

In view of the current state of the art described above, the present invention aims to provide a method for producing an asymmetric chain carbonate by reacting an alcohol with a halocarbonate ester compound at a high conversion rate and high selectivity.

Solution to Problem

The present invention relates to a method for producing an asymmetric chain carbonate, the method including
reacting an alcohol represented by Formula (1):

$$R^1OH$$

wherein $R^1$ is an organic group,
with a halocarbonate ester compound represented by Formula (2):

$$XCOOR^2$$

wherein X is a halogen atom; and $R^2$ is an organic group different from $R^1$,
in the presence of a basic magnesium salt or a basic alkaline earth metal salt to produce an asymmetric chain carbonate represented by Formula (3):

$$R^1OCOOR^2$$

wherein $R^1$ and $R^2$ are as defined above (hereinafter, also referred to as "first production method of the present invention" or "first production method").

In the first production method of the present invention, preferably, $R^1$ is an alkyl group having no fluorine atom or an alkyl group having a fluorine atom, and $R^2$ is an alkyl group having no fluorine atom or an alkyl group having a fluorine atom.

The present invention also relates to a method for producing an asymmetric chain carbonate, the method including
reacting an alcohol represented by Formula (1):

$$R^1OH$$

wherein $R^1$ is an organic group,
with a halocarbonate ester compound represented by Formula (2):

$$XCOOR^2$$

wherein X is a halogen atom; and $R^2$ is an organic group different from $R^1$,
in the presence of an inorganic base and a desiccant to produce an asymmetric chain carbonate represented by Formula (3):

$$R^1OCOOR^2$$

wherein $R^1$ and $R^2$ are as defined above (hereinafter, also referred to as "second production method of the present invention" or "second production method").

In the second production method of the present invention, preferably, $R^1$ is an alkyl group having no fluorine atom or an alkyl group having a fluorine atom, and $R^2$ is an alkyl group having no fluorine atom or an alkyl group having a fluorine atom.

The inorganic base in the second production method of the present invention is preferably at least one selected from the group consisting of carbonates of alkali metals, hydroxides of alkali metals, oxides of magnesium, oxides of alkaline earth metals, hydroxides of magnesium, hydroxides of alkaline earth metals, carbonates of magnesium, carbonates of alkaline earth metals, acetates of magnesium, and acetates of alkaline earth metals.

The desiccant in the second production method of the present invention is preferably at least one selected from the group consisting of neutral calcium salts, zeolite, silica gel, alumina, and activated carbon.

The present invention also relates to a composition including:
an asymmetric chain carbonate represented by Formula (3):

$$R^1OCOOR^2$$

wherein $R^1$ is an organic group; and $R^2$ is an organic group different from $R^1$, and
at least one selected from the group consisting of symmetric chain carbonates represented by Formula (4):

$$R^1OCOOR^1$$

wherein $R^1$ is as defined above; and symmetric chain carbonates represented by Formula (5):

$$R^2OCOOR^2$$

wherein $R^2$ is as defined above (hereinafter, also referred to as "first composition of the present invention" or "first composition").

The present invention also relates to a composition including:
an asymmetric chain carbonate represented by Formula (3):

$$R^1OCOOR^2$$

wherein $R^1$ is an organic group; and $R^2$ is an organic group different from $R^1$, and
water,
the composition containing water in an amount of 100 ppm or less (hereinafter, also referred to as "second composition of the present invention" or "second composition").

Advantageous Effects of Invention

The first and second production methods of the present invention with the above-described features enable production of an asymmetric chain carbonate by reacting an alcohol with a halocarbonate ester compound at a high conversion rate and high selectivity.

DESCRIPTION OF EMBODIMENTS

The present invention will be specifically described below.

The first production method is a method for producing an asymmetric chain carbonate represented by Formula (3) by reacting an alcohol represented by Formula (1) with a halocarbonate ester compound represented by Formula (2) in the presence of a basic magnesium salt or a basic alkaline earth metal salt. The present inventors have found that a high conversion rate and high selectivity can be surprisingly achieved by the use of a basic magnesium salt or a basic alkaline earth metal salt.

Examples of the basic magnesium salt or basic alkaline earth metal salt include basic magnesium salts such as magnesium oxide, magnesium hydroxide, magnesium carbonate, magnesium hydrogen carbonate, and magnesium acetate; basic calcium salts such as calcium oxide, calcium hydroxide, calcium carbonate, calcium hydrogen carbonate, and calcium acetate; basic strontium salts such as strontium oxide, strontium hydroxide, strontium carbonate, strontium hydrogen carbonate, and strontium acetate; basic barium salts such as barium oxide, barium hydroxide, barium carbonate, barium hydrogen carbonate, and barium acetate; and mixtures thereof.

The basic magnesium salt or basic alkaline earth metal salt is preferably a basic calcium salt. Usually, a weak acid calcium salt is used. In particular, it is more preferably at least one selected from the group consisting of calcium oxide, calcium hydroxide, calcium carbonate, calcium hydrogen carbonate, and calcium acetate.

The amount of the basic calcium salt or basic alkaline earth metal salt per mol of the alcohol represented by Formula (1) is preferably 0.5 to 2.0 mol, and is more preferably 0.7 mol or more and more preferably 1.5 mol or less. In the case of using two or more salts, the amount means the total amount of all the salts.

The purity of the basic calcium salt or basic alkaline earth metal salt is not particularly limited, but is preferably 90% by mass or higher to keep expected reactivity. Usually, no other salt is used, but other neutral or basic inorganic salts may be contained.

The calcium oxide may contain impurities such as hydrochloric acid-insoluble substances, chlorides, carbonates, sulfates, heavy metals, and iron, but a smaller amount is better. For example, acceptable amounts of impurities are as follows.
Hydrochloric acid-insoluble substance: 0.5% or less
Chloride (Cl): 0.25% or less
Carbonate: test-passed amount (forming almost no bubbles)
Sulfate ($SO_4$): 1.0% or less
Heavy metal (Pb): 0.025% or less
Iron (Fe): 0.25% or less The calcium oxide preferably has an ignition loss (800° C.) of 6.0% or less. The calcium oxide content (after ignition) is preferably 98.0% or more.

The calcium hydroxide preferably has a purity of 96.0% or higher. The calcium hydroxide may contain impurities such as hydrochloric acid-insoluble substances, carbonates, chlorides, sulfates, sodium, potassium, magnesium, lead, arsenicum, chromium, manganese, and iron, but a smaller amount is better. For example, acceptable amounts of impurities are as follows.
Hydrochloric acid-insoluble substance: 0.5% or less
Carbonate: test-passed amount (forming almost no bubbles)
Chloride (Cl): 0.05% or less
Sulfate ($SO_4$): 0.25% or less
Sodium (Na): 0.25% or less
Potassium (K): 0.25% or less
Magnesium (Mg): 5.0% or less
Lead (Pb): 0.015% or less
Arsenicum (As): 2.5 ppm or less
Chromium (Cr): 0.025% or less
Manganese (Mn): 0.05% or less
Iron (Fe): 0.10% or less The calcium hydroxide preferably meets the standard prescribed in JIS K 8575-1994.

In the first production method, the below-described desiccant is not essential, but may be used.

The second production method is a method for producing an asymmetric chain carbonate represented by Formula (3) by reacting an alcohol represented by Formula (1) with a halocarbonate ester compound represented by Formula (2) in the presence of an inorganic base and a desiccant. The present inventors have found that a high conversion rate and high selectivity can be surprisingly achieved by the use of an inorganic base and a desiccant.

Preferably, the inorganic base is at least one selected from the group consisting of carbonates of alkali metals, hydroxides of alkali metals, oxides of magnesium, oxides of alkaline earth metals, hydroxides of magnesium, hydroxides of alkaline earth metals, carbonates of magnesium, carbonates of alkaline earth metals, acetates of magnesium, and acetates of alkaline earth metals. More preferably, it is at least one selected from the group consisting of potassium carbonate, sodium carbonate, potassium hydroxide, and sodium hydroxide.

The amount of the inorganic base per mol of the alcohol represented by Formula (1) is preferably 0.5 to 2.0 mol, and is more preferably 0.7 mol or more and more preferably 1.5 mol or less.

The desiccant is preferably at least one selected from the group consisting of neutral calcium salts, zeolite, silica gel, alumina, and activated carbon, more preferably at least one selected from the group consisting of calcium chloride, zeolite, and alumina.

The neutral calcium salt usually means a strong acid calcium salt. It is preferably at least one selected from the group consisting of calcium chloride, calcium bromide, calcium iodide, and calcium sulfate.

The purity of the neutral calcium salt is not particularly limited, but is preferably 90% by mass or higher to keep expected reactivity. Usually, no other salt is used, but other neutral or basic inorganic salts may be contained.

Each neutral calcium salt may be used alone or in combination of two or more.

The neutral calcium salt may be activated before use. The activation is performed, for example, by drying treatment with heating at 300° C. to 350° C. or at 350° C. to 400° C. overnight in vacuum ($10^{-1}$ to $10^{-3}$ mmHg). Neutral calcium salts not activated by such a treatment can also be suitably used.

The zeolite may be natural zeolite or a synthesized zeolite.

The zeolite is preferably a synthesized zeolite.

The zeolite is preferably one represented by the formula: $M_{2/n}O \cdot Al_2O_3 \cdot xSiO_2 \cdot yH_2O$ (wherein M represents a metal cation, n represents the valence of the metal cation, x represents a coefficient, and y represents a coefficient). The metal cation as M is preferably at least one metal cation selected from the group consisting of a sodium cation, a lithium cation, and a potassium cation.

The zeolite is preferably porous.

The zeolite preferably has an average pore size of preferably 3 to 5 angstrom, more preferably 3 to 4 angstrom.

The morphology of the zeolite may be, for example, powder, granule, or pellet, and is preferably powder or granule.

The zeolite has a weight average particle diameter of preferably 10 μm or less, more preferably 5 μm or less. Herein, the particle diameter refers to a major axis. Herein, in the case where the primary particles of zeolite form secondary particles, the term "weight average particle diameter" refers to the particle diameter of the secondary particles.

Each zeolite may be used alone or in combination of two or more.

The zeolite may be activated before use. The activation is performed, for example, by drying treatment with heating at 300° C. to 350° C. overnight in vacuum ($10^{-1}$ to $10^{-3}$ mmHg). Zeolite not activated by such a treatment can also be suitably used.

The silica gel may be spherical or crushed silica gel.

In the case of spherical silica gel, the particle diameter thereof upon use does not matter, but is more preferably about 40 to 500 μm.

The silica gel may be acid silica gel, neutral silica gel, or basic silica gel such as amino silica.

Each silica gel may be used alone or in combination of two or more.

The silica gel may be activated before use. The activation is performed, for example, by drying treatment with heating at 300° C. to 350° C. overnight in vacuum ($10^{-1}$ to $10^{-3}$ mmHg). Silica gel not activated by such a treatment can also be suitably used.

Alumina having any shape may be used.

The particle diameter of the alumina upon use does not matter, but is preferably about 50 to 100 μm.

The alumina may be acid alumina, neutral alumina, or basic alumina.

Each alumina may be used alone or in combination of two or more.

The alumina may be activated before use. The activation is performed, for example, by drying treatment with heating at 100° C. to 150° C. overnight in vacuum ($10^{-1}$ to $10^{-3}$ mmHg). Almina not activated by such a treatment can also be suitably used.

The activated carbon may be crushed, granulated, or molded activated carbon.

In the case of spherical activated carbon, the particle diameter thereof does not matter, but is more preferably about 50 to 100 μm.

The activated carbon may be gas-activated carbon, zinc chloride-activated carbon, or phosphoric acid-activated carbon.

Each activated carbon may be used alone or in combination of two or more.

The activated carbon may be activated before use. The activation is performed, for example, by firing at 800° C. to 1000° C. Activated carbon not having undergone such a treatment can also be suitably used.

The alcohol is represented by Formula (1):

$$R^1OH$$

wherein $R^1$ is an organic group.

Examples of the organic group include alkyl groups optionally having one or more substituent(s), alkenyl groups optionally having one or more substituent(s), alkynyl groups optionally having one or more substituent(s), cycloalkyl groups optionally having one or more substituent(s), cycloalkenyl groups optionally having one or more substituent(s), aryl groups optionally having one or more substituent(s), and heteroaryl groups optionally having one or more substituent(s).

The organic group is preferably an alkyl group optionally having one or more substituent(s) or an aryl group optionally having one or more substituent(s).

Examples of the substituent include halogen atoms (preferably, fluorine atom), alkyl groups, fluorinated alkyl groups, aryl groups, and heteroatom-containing groups. Preferred of these is a halogen atom, and more preferred is a fluorine atom. Examples of the heteroatom-containing groups include groups containing N, O, or S, such as an amino group, an amide group, a hydroxy group, an ether bond, an ester bond, a thiol bond, and a SH group.

The number of the substituents is preferably 1 to 4, more preferably 1 to 3, still more preferably 1 or 2.

The organic group is preferably an optionally substituted alkyl group.

The organic group may be an alkyl group having no halogen atom or an alkyl group having a halogen atom, or may be an alkyl group having no fluorine atom or an alkyl group having a fluorine atom.

The organic group is more preferably an alkyl group having a halogen atom, still more preferably an alkyl group having a fluorine atom.

The organic group has preferably 20 or less carbon atoms, more preferably 10 or less carbon atoms, still more preferably five or less carbon atoms, particularly preferably three or less carbon atoms, most preferably two or less carbon atoms, and may have one or more carbon atoms.

The alkyl group has preferably 20 or less carbon atoms, more preferably 10 or less carbon atoms, still more preferably five or less carbon atoms, particularly preferably three or less carbon atoms, most preferably two or less carbon atoms, and may have one or more carbon atoms.

The alkyl group may be linear or branched.

Examples of $R^1$ include —$CH_3$, —$CH_2CH_3$, —$CH_2$—O—$CH_3$, —$CH_2$—$CH_2$—O—$CH_3$, —$C_6H_5$, —$CF_3$, —$CF_2H$, —$CFH_2$, —$CH_2CF_3$, —$CH_2CF_2H$, —$CH_2CFH_2$, —$CF_2CF_3$, —$CF_2CF_2H$, —$CF_2CFH_2$, —$CFHCF_3$, —$CFHCF_2H$, —$CFHCFH_2$, —$CH(CF_3)_2$, —$CH_2C_2F_5$, —$CH_2CF_2CF_3$, —$CH_2CF_2CF_2H$, —$CF_2CF_2CF_3$, —$CHFCH_3$, and —$CF_2CH_3$.

In particular, in order to achieve a high conversion rate and high selectivity, $R^1$ is preferably a C1-C3 alkyl group having a fluorine atom, more preferably at least one selected from the group consisting of —$CF_3$, —$CF_2H$, —$CFH_2$, —$CH_2CF_3$, —$CH_2CF_2H$, —$CH_2CFH_2$, —$CF_2CF_3$, —$CF_2CF_2H$, —$CF_2CFH_2$, —$CFHCF_3$, —$CFHCF_2H$, —$CFHCFH_2$, —$CH(CF_3)_2$, —$CH_2C_2F_5$, —$CH_2CF_2CF_3$, —$CH_2CF_2CF_2H$, and —$CF_2CF_2CF_3$, still more preferably at least one selected from the group consisting of —$CH_2CF_3$ and —$CF_2CF_3$.

The halocarbonate ester compound is represented by Formula (2):

wherein X is a halogen atom, and $R^2$ is an organic group different from $R^1$.

The halogen atom as X is preferably F, Cl, Br, or I, more preferably F or Cl, still more preferably Cl.

The halocarbonate ester compound to be used has a purity of 95 to 100% by mass, and may be used without undergoing any treatment or after purified by a usual method such as dehydration or distillation. Unpurified halocarbonate ester compounds may also be suitably used.

$R^2$ is an organic group different from $R^1$.

Examples of the organic group include alkyl groups optionally having one or more substituent(s), alkenyl groups optionally having one or more substituent(s), alkynyl groups optionally having one or more substituent(s), cycloalkyl groups optionally having one or more substituent(s), cycloalkenyl groups optionally having one or more substituent(s), aryl groups optionally having one or more substituent(s), and heteroaryl groups optionally having one or more substituent(s).

The organic group as $R^2$ is preferably an alkyl group optionally having one or more substituent(s) or an aryl group optionally having one or more substituent(s).

Examples of the substituent include halogen atoms (preferably, fluorine atom), alkyl groups, fluorinated alkyl groups, aryl groups, and heteroatom-containing groups.

Examples of heteroatom-containing groups include groups containing N, O, or S, such as an amino group, an amide group, a hydroxy group, an ether bond, an ester bond, a thiol bond, and a SH group.

The number of the substituents is preferably 1 to 4, more preferably 1 to 3.

The organic group as $R^2$ is preferably an optionally substituted alkyl group.

The organic group as $R^2$ may be an alkyl group having no halogen atom or an alkyl group having a halogen atom, or may be an alkyl group having no fluorine atom or an alkyl group having a fluorine atom.

The organic group as $R^2$ has preferably 20 or less carbon atoms, more preferably 10 or less carbon atoms, still more preferably five or less carbon atoms, particularly preferably three or less carbon atoms, most preferably two or less carbon atoms, and may have one or more carbon atoms.

The alkyl group has preferably 20 or less carbon atoms, more preferably 10 or less carbon atoms, still more preferably five or less carbon atoms, particularly preferably three or less carbon atoms, most preferably two or less carbon atoms, and may have one or more carbon atoms.

The alkyl group may be linear or branched.

Examples of $R^2$ include —$CH_3$, —$CH_2CH_3$, —$CH(CH_3)_2$, —$CH_2CF_3$, and —$CH_2C_2H_5$.

In particular, in order to achieve a high conversion rate and high selectivity, $R^2$ is preferably a C1-C3 alkyl group having no fluorine atom, more preferably at least one selected from the group consisting —$CH_3$, —$CH_2CH_3$, —$CH(CH_3)_2$, and —$CH_2C_2H_5$, still more preferably —$CH_3$.

In order to achieve a high conversion rate and high selectivity, preferably at least one of $R^1$ and $R^2$ is an alkyl group having a halogen atom. More preferably, one of $R^1$ and $R^2$ is an alkyl group having a halogen atom, and the other is an alkyl group having no halogen atom.

In order to achieve a high conversion rate and high selectivity, preferably at least one of $R^1$ and $R^2$ is an alkyl group having a fluorine atom. More preferably, one of $R^1$ and $R^2$ is an alkyl group having a fluorine atom, and the other is an alkyl group having no fluorine atom.

The asymmetric chain carbonate is represented by Formula (3):

wherein $R^1$ and $R^2$ are as defined above.

The first and second production methods are particularly suitable to produce an asymmetric chain carbonate such as $CF_3OCOOCH_3$, $CF_3CH_2OCOOCH_3$, $CF_3CF_2OCOOCH_3$, $CF_3CF_2CF_2OCOOCH_3$, $CF_3CF(CF_3)OCOOCH_3$, $CF_3CH(CF_3)OCOOCH_3$, $CF_3CF(CH_3)OCOOCH_3$, $CF_3CH(CH_3)OCOOCH_3$, $CF_3OCOOCH_2CH_3$, $CF_3CH_2OCOOCH_2CH_3$, $CF_3CF(CF_3)OCOOCH_2CH_3$, $CF_3CH(CF_3)OCOOCH_2CH_3$, $CF_3CF(CH_3)OCOOCH_2CH_3$, $CF_3CH(CH_3)OCOOCH_2CH_3$, $CH_3OCOOCFHCH_3$, and $CH_3CH_2OCOOCFHCH_3$.

The reactions in the first and second production methods may be performed in a solvent, but use of a solvent is not essential. Use of a solvent is advantageous in facilitating mixing of raw materials and removal of heat generated in the reactions. Use of no solvent is advantageous in simplifying collection of target products and cost efficiency.

The solvent is preferably an organic solvent. Use of water as a solvent may lead to an insufficient conversion rate.

Examples of the solvent include esters such as methyl acetate, ethyl acetate, propyl acetate, n-butyl acetate, and tert-butyl acetate; ketones such as acetone, methyl ethyl ketone, and cyclohexanone; aliphatic hydrocarbons such as hexane, cyclohexane, octane, nonane, decane, undecane, dodecane, and mineral spirits; aromatic hydrocarbons such as benzene, toluene, xylene, naphthalene, and solvent naphtha; alcohol such as methanol, ethanol, tert-butanol, isopropanol, and ethyleneglycol monoalkyl ethers; chain ethers such as dimethyl ether and diethyl ether; cyclic ethers such as tetrahydrofuran, tetrahydropyran, and dioxane; halogenated hydrocarbons such as chloromethane, dichloromethane, trichloromethane (chloroform), tetrachloromethane, 1,2-dichloroethane, and difluoroethane; amides such as N-methylpyrrolidone, dimethylformamide, and dimethylacetamide; nitriles such as acetonitrile; and sulfoxides such as dimethyl sulfoxide.

In particular, the solvent is preferably at least one selected from the group consisting of dodecane, octane, nonane, decane, dichloromethane, 1,2-dichloroethane, chloroform, carbon tetrachloride, toluene, xylene, ethyl acetate, propyl acetate, and butyl acetate. If the target carbonate is liquid, such a solvent is preferred in view of simplification of the reaction system.

The reaction temperature is preferably −20° C. to 40° C., more preferably −10° C. to 30° C., still more preferably 0° C. to 20° C. At too high a reaction temperature, the halocarbonate ester compound represented by Formula (2) may be deactivated.

The duration of the reaction is preferably 0.1 to 100 hours, more preferably 1 to 90 hours, still more preferably 5 to 80 hours.

The reaction may be performed at atmospheric pressure or elevated pressure, for example, at 1 MPa (gauge pressure) or lower.

The first and second production methods may further include distillation of the asymmetric chain carbonate produced by the reaction.

The first composition of the present invention includes:
an asymmetric chain carbonate represented by Formula (3):

$$R^1OCOOR^2$$

wherein $R^1$ is an organic group; and $R^2$ is an organic group different from $R^1$, and
at least one selected from the group consisting of symmetric chain carbonates represented by Formula (4):

$$R^1OCOOR^1$$

wherein $R^1$ is as defined above; and symmetric chain carbonates represented by Formula (5):

$$R^2OCOOR^2$$

wherein $R^2$ is as defined above.

The definitions of $R^1$ and $R^2$ are as described for the first and second production methods.

The amount of the asymmetric chain carbonate represented by Formula (3) relative to the composition is preferably 30 to 99.99% by mass, more preferably 50 to 99.95% by mass, still more preferably 80 to 99.9% by mass.

The amount of the symmetric chain carbonate represented by Formula (4) relative to the composition is preferably 0.01 to 10% by mass, more preferably 0.05 to 5% by mass, still more preferably 0.1 to 2% by mass.

The amount of the symmetric chain carbonate represented by Formula (5) relative to the composition is preferably 0.01 to 10%, more preferably 0.05 to 5% by mass, still more preferably 0.1 to 2% by mass.

The amounts of the symmetric or asymmetric chain carbonates represented by Formula (3) to Formula (5) can be measured by gas chromatography.

The first composition can be produced by the first and second production methods.

The second composition of the present invention includes:
an asymmetric chain carbonate represented by Formula (3):

$$R^1OCOOR^2$$

wherein $R^1$ is an organic group; and $R^2$ is an organic group different from $R^1$, and
water,
the composition containing water in an amount of 100 ppm or less.

The definitions of $R^1$ and $R^2$ are as described for the first and second production methods.

The amount of water can be measured using a Karl Fischer moisture meter.

The second composition can be produced by the first and second production methods.

EXAMPLES

The present invention will be specifically described below with reference to, but not limited to, examples.

Example 1

Stirring of 2,2,2-trifluoroethanol (1 g, 10 mmol), calcium oxide (560 mg, 10 mmol), and dichloromethane (2.84 g, 30 mmol) was performed at 0° C. to 5° C. To the resulting mixture was carefully dropwise added methyl chloroformate (0.992 g, 10.5 mmol) while preventing heat generation. After the completion of the dropping, the mixture was stirred for about 16 hours while gradually raising the temperature to room temperature, and then filtrated and distilled, thereby producing a composition containing $CF_3CH_2OCOOCH_3$ and $CH_3OCOOCH_3$ with a conversion rate of 99.0%. The conversion rate means the conversion rate of the alcohol (2,2,2-trifluoroethanol in Example 1) determined by gas chromatography (GC). Table 1 shows the result. With regard to the water content of the system, the composition produced by the reaction was pulled out with a dry syringe and subjected to measurement using a Karl Fischer moisture meter to confirm that the composition contained water in an amount of 22 ppm (average of three measures).

Example 2

A composition containing $CF_3CH_2OCOOCH_3$ and $CH_3OCOOCH_3$ was produced as in Example 1, except that calcium hydroxide was used instead of calcium oxide. The conversion rate was 99.9%. The water content was measured using a Karl Fischer moisture meter and confirmed to be 85 ppm (average of three measures).

Example 3

A composition containing $CF_3CH_2OCOOCH_3$ and $CH_3OCOOCH_3$ was produced as in Example 1, except for using no dichloromethane. The conversion rate was 95.4%.

Comparative Example 1

The same operation as in Example 1 was performed, except that pyridine was used instead of calcium oxide. The conversion rate was only 24.0%. The methyl chloroformate was decomposed. A lot of symmetric carbonate was observed.

Example 4

A composition containing $CF_3CH_2OCOOCH_3$ and $CH_3OCOOCH_3$ was produced as in Example 1, except that methanol, trifluoroethyl chloroformate, and calcium hydroxide were used instead of 2,2,2-trifluoroethanol, methyl chloroformate, and calcium oxide, respectively. The conversion rate was 99.6%.

Example 5

A composition containing $CH_3CH_2OCOOCH_3$ and $CH_3OCOOCH_3$ was produced as in Example 1, except that ethanol and calcium hydroxide were used instead of 2,2,2-trifluoroethanol and calcium oxide, respectively. The conversion rate was 99.3%.

Example 6

A composition containing $CH_3OCH_2CH_2OCOOCH_3$ and $CH_3OCOOCH_3$ was produced as in Example 1, except that 2-methoxy ethanol and calcium hydroxide were used instead of 2,2,2-trifluoroethanol and calcium oxide, respectively. The conversion rate was 99.4%.

Example 7

A composition containing $C_6H_5OCOOCH_3$ and $CH_3OCOOCH_3$ was produced as in Example 1, except that phenol and calcium hydroxide were used instead of 2,2,2-trifluoroethanol and calcium oxide, respectively. The conversion rate was 99.0%.

Example 8

Stirring of 2,2,2-trifluoroethanol (1 g, 10 mmol), potassium carbonate (1.38 g), calcium chloride (1.11 mg, 10 mmol), and dichloromethane (2.84 g, 30 mmol) was performed at 0° C. to 5° C. To the resulting mixture was carefully dropwise added methyl chloroformate (0.992 g, 10.5 mmol) while preventing heat generation. After the completion of the dropping, the mixture was stirred for about 16 hours while gradually raising the temperature to room temperature, and then filtrated and distilled, thereby producing a composition containing $CF_3CH_2OCOOCH_3$ and $CH_3OCOOCH_3$ with a conversion rate of 94.8%.

Comparative Example 2

The same operation as in Example 4 was performed, except that pyridine was used instead of calcium hydroxide. The conversion rate was only 34.3%. The trifluoroethyl chloroformate was decomposed. A lot of symmetric carbonate was observed.

Comparative Example 3

The same operation as in Example 5 was performed, except that pyridine was used instead of calcium hydroxide. The conversion rate was only 36.6%. The methyl chloroformate was decomposed. A lot of symmetric carbonate was observed.

Comparative Example 4

The same operation as in Example 8 was performed, except for adding no calcium chloride. The conversion rate was only 31.4%. The methyl chloroformate was decomposed. A lot of symmetric carbonate was observed.

The selectivity in the following table was determined based on the area ratios measured by gas chromatography.

TABLE 1

| | GC area % | | | | Conversion rate % | Selectivity % |
|---|---|---|---|---|---|---|
| | $R^1OH$ | $CH_3OCOCl$ | $CH_3OCOOCH_3$ | $R^1OCOOCH_3$ | | |
| Example 1 | 0.98 | 0.91 | 1.42 | 96.69 | 99.0 | 98.6 |
| Example 2 | 0.12 | 1.11 | 1.47 | 97.30 | 99.9 | 98.5 |
| Example 3 | 4.55 | 0.74 | 0.85 | 93.86 | 95.4 | 99.1 |
| Example 4 | 0.35 | 0.88 | 1.39 | 96.88 | 99.6 | 98.5 |
| Example 5 | 0.69 | 2.08 | 1.51 | 95.72 | 99.3 | 98.4 |
| Example 6 | 0.55 | 1.82 | 1.43 | 96.20 | 99.4 | 98.5 |
| Example 7 | 0.99 | 1.67 | 1.88 | 95.72 | 99.0 | 98.1 |
| Example 8 | 4.20 | 17.17 | 1.38 | 77.25 | 94.8 | 98.2 |
| Comparative Example 1 | 57.33 | 0.00 | 24.55 | 18.12 | 24.0 | 42.4 |
| Comparative Example 2 | 48.78 | 0.00 | 25.80 | 25.42 | 34.3 | 49.6 |
| Comparative Example 3 | 50.18 | 0.00 | 20.89 | 28.99 | 36.6 | 58.1 |
| Comparative Example 4 | 49.24 | 0.00 | 28.17 | 22.59 | 31.4 | 44.5 |

The invention claimed is:

1. A composition comprising:
   (A) 80 to 99.99% by mass of an asymmetric chain carbonate represented by Formula (3):

$$R^1OCOOR^2 \quad (3),$$

wherein, in Formula (3), $R^1$ is an organic group; and $R^2$ is an organic group different from $R^1$, and
   (B) at least one selected from the group consisting of symmetric chain carbonates represented by Formula (4):

$$R^1OCOOR^1 \quad (4),$$

wherein, in Formula (4), $R^1$ is as defined above; and symmetric chain carbonates represented by Formula (5):

$$R^2OCOOR^2 \quad (5),$$

wherein, in Formula (5), $R^2$ is as defined above, and
   (C) a halocarbonate ester compound represented by Formula (2):

$$XCOOR^2 \quad (2)$$

wherein, in Formula (2), X is a halogen atom, and $R^2$ is as defined above; and
   wherein the asymmetric chain carbonate represented by Formula (3) is at least one selected from the group consisting of $CF_3OCOOCH_3$, $CF_3CH_2OCOOCH_3$, $CF_3CF_2OCOOCH_3$, $CF_3CF_2CF_2OCOOCH_3$, $CF_3CF(CF_3)OCOOCH_3$, $CF_3CH(CF_3)OCOOCH_3$, $CF_3CF(CH_3)OCOOCH_3$, $CF_3CH(CH_3)OCOOCH_3$, $CF_3OCOOCH_2CH_3$, $CF_3CH_2OCOOCH_2CH_3$, $CF_3CF(CF_3)OCOOCH_2CH_3$, $CF_3CH(CF_3)OCOOCH_2CH_3$, $CF_3CF(CH_3)OCOOCH_2CH_3$, $CF_3CH(CH_3)OCOOCH_2CH_3$, $CH_3OCOOCFHCH_3$, and $CH_3CH_2OCOOCFHCH_3$.

2. The composition of claim 1, further comprising an alcohol represented by Formula (1):

$$R^1OH$$

wherein, in Formula (1), $R^1$ is as defined in claim 1.

* * * * *